United States Patent
Yu et al.

(10) Patent No.: US 8,802,409 B2
(45) Date of Patent: Aug. 12, 2014

(54) MICROBIAL OIL PRODUCTION FROM BIOMASS HYDROLYSATE BY OLEAGINOUS YEAST STRAINS

(75) Inventors: Xiaochen Yu, Pullman, WA (US); Yubin Zheng, Pullman, WA (US); Shulin Chen, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 13/225,656

(22) Filed: Sep. 6, 2011

(65) Prior Publication Data

US 2012/0083023 A1  Apr. 5, 2012

Related U.S. Application Data

(60) Provisional application No. 61/380,259, filed on Sep. 6, 2010.

(51) Int. Cl.
*C12P 1/02* (2006.01)

(52) U.S. Cl.
USPC .......................................... 435/171

(58) Field of Classification Search
None
See application file for complete search history.

(56) References Cited

U.S. PATENT DOCUMENTS

| | | | | |
|---|---|---|---|---|
| 4,461,648 A | * | 7/1984 | Foody | 127/37 |
| 2009/0217569 A1 | * | 9/2009 | Pastinen et al. | 44/308 |

* cited by examiner

*Primary Examiner* — Suzanne M Noakes
*Assistant Examiner* — Stephen Chong
(74) *Attorney, Agent, or Firm* — Whitham, Curtis, Christofferson & Cook, P.C.

(57) ABSTRACT

Oleaginous yeast strains are used to hydrolyze biomass (e.g. wheat straw) that has been pretreated using dilute acid, in order to produce lipids. The lipids may be used as feedstock for producing biofuels.

16 Claims, 1 Drawing Sheet

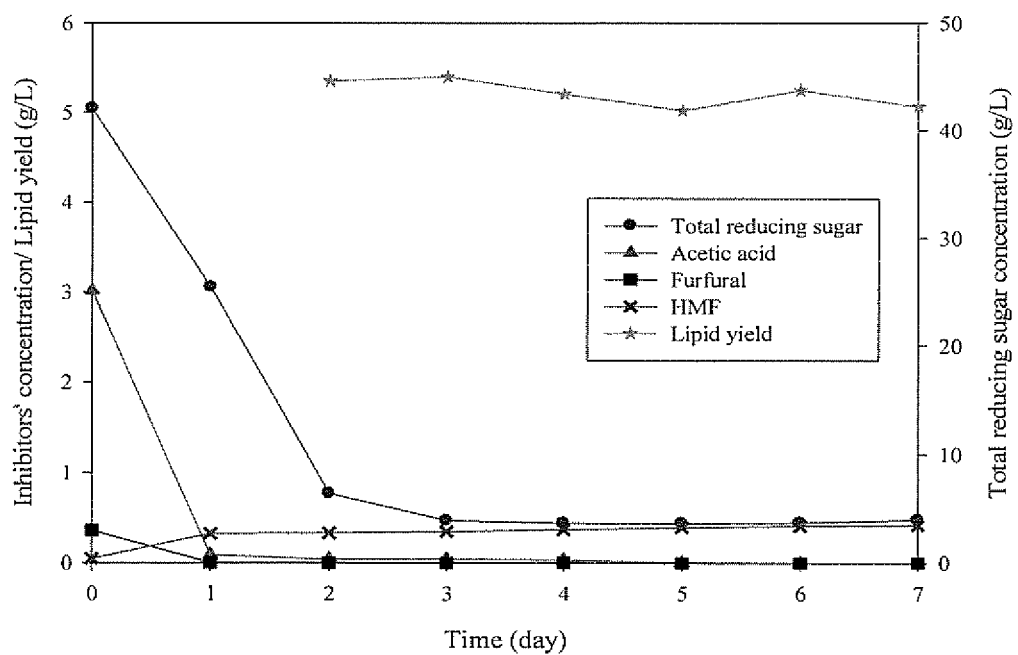

MICROBIAL OIL PRODUCTION FROM BIOMASS HYDROLYSATE BY OLEAGINOUS YEAST STRAINS

CROSS-REFERENCE TO RELATED APPLICATIONS

This application claims benefit of U.S. provisional patent application 61/380,259 filed Jun. 6, 2010, the complete contents of which is hereby incorporated by reference.

BACKGROUND OF THE INVENTION

1. Field of the Invention

The invention relates to an effective and economical strategy for lipid production. In particular, oleaginous yeast strains are used to hydrolyze biomass (e.g. wheat straw) that has been pretreated using dilute acid, in order to produce lipids. The lipids may be used as feedstock for producing biofuels.

2. Background of the Invention

Bio-fuel with its potential as a clean and renewable alternative to conventional fossil fuels has received increasing focus in recent years (Huang et al., 2009). However, successful bio-fuel commercialization economics depend on both large quantities and low cost of the feedstock. Lignocellulosic materials, due to their abundance and sustainability, have been attracting the attention of the bio-fuel production industry.

Wheat straw is an abundant by-product from wheat production. The average yield of wheat straw is 1.3-1.4 lb per lb of wheat grain (Montane et al., 1998). Based on the data from Food and Agricultural Organization, 55.8 million metric tons of wheat were produced in the USA in 2007 (world production, 606.0 million metric tons) (FAO, 2007). Wheat straw contains 35-45% cellulose, 20-30% hemicellulose and 8-15% lignin. And both cellulose and hemicellulose as the main components can be converted to fermentable pentoses and hexoses for bio-fuel production.

Due to the natural stability and resistance-to-bond-breaking properties of lignocellulosic materials, dilute acid pretreatment applied prior to hemicellulose hydrolysis greatly increases the effectiveness of the subsequent enzyme hydrolysis. The combination of acid pretreatment and enzymatic hydrolysis leads to the production of pentose and hexose species in the hydrolysate resulted from the dissolution of the hemicellulose.

The utilization of both pentose and hexose sugars present in dilute acid pretreated biomass hydrolysate is essential for economical bio-fuel production (Saha et al., 2005). Pentose, mainly xylose from hemicellulose, can be utilized for ethanol production by some either naturally occurring or genetically engineered strains such as, *Thermoanaerobacter mathranii, Candida shehatae, Pachysolen tannophihts, Pichia stipitis, Saccharomyces Cerevisiae, Zymomonas mobilis* and *Escherichia coli* (Agbogbo and Coward-Kelly, 2008; Ahring et al., 1998; Fu and Peiris, 2008). Hexose both from cellulose and hemicellulose is most widely used by *S. cerevisia*, which can give high ethanol yields and productivities in addition to a high ethanol tolerance (Olsson and Hahn-Haegerdal, 1996). However, *S. cerevisia* is unable to produce ethanol from xylose unless it is genetically engineered. Even in that case, low ethanol yield and the adverse effect of inhibitors contained in the hydrolysate often create technical challenges in using the process.

There is an ongoing need to develop new, improved and yet economical pocesses that use renewable lignocellulosic biomass to produce biofuels. In such processes, high efficiency utilization of pentose as well as hexose is required.

SUMMARY OF THE INVENTION

The invention provides efficient and economical methods of synthesizing lipids for use in the production of biofuels. According to the invention, biomass is hydrolyzed using dilute acid, and saccharides (e.g. pentose and hexose species) from the biomass hydrolysate are converted into lipids by oleaginous yeast strains, such as *Cryptococcus curvatus, Rhodotorula glutinis* and *Trichosporon fermentans*, etc. The lipids are useful, for example, for the production of biofuel.

BRIEF DESCRIPTION OF THE DRAWINGS

FIG. 1. Total reducing sugars and inhibitors consumptions in the non-detoxified liquid hydrolysate (NDLH) during fermentation by *C. curvatus*.

DETAILED DESCRIPTION OF THE INVENTION

Dilute acid pretreatment of lignocellulosic biomass is known to convert hemicelluloses in biomass to a hydrolysate mainly composed of pentoses, some glucose from celluloses and other degradation products. Conventional dilute acid hydrolysis is carried out in two stages to maximize sugar yields from the hemicellulose and cellulose fractions of biomass. The first stage is operated under milder conditions to hydrolyze hemicellulose, while the second stage is optimized to hydrolyze the more resistant cellulose fraction. Liquid hydrolysates are recovered from each stage, neutralized, and fermented to products such as ethanol. Unfortunately, products formed during hydrolysis usually cause inhibition of engineered organisms during the fermentation process, resulting in low levels of products such as ethanol. The present invention provides an alternative use of the hydrolysate sugars from dilute acid hydrolysis for microbial oil production. As described herein, sugars in hydrolysate obtained from dilute sulfuric acid pretreatment of biomass can be used by oleaginous yeasts strains to synthesize lipids, even with no further treatment. The experimental results showed that all oleaginous strains tested could use both overlimed, detoxified and non-detoxified hydrolysates to produce lipids. Surprisingly, the non-detoxified hydrolysate had no significantly negative impact on the growth of the selective yeast strains except for one: *Rhodosporidium toruloides*. *C. curvatus* had the best performance on both the detoxified and non-detoxified hydrolysates. This invention thus provides a feasible strategy to utilize hydrolysate from pretreating biomass with dilute acid for microbial oil production with or without detoxification. In addition, residual solids with most of the cellulose can, after further enzymatic hydrolysis, also be used for the production of either oil or other valuable products, such as ethanol.

By "biomass" we mean biological materials from living or recently living plants, including agricultural waste products. Lignocellulosic biomass typically comprises cellulose and hemicellulose, and the biomass that is pretreated using dilute acid can be any suitable biomass that contains cellulose and hemicellulose, and that is susceptible to dilute acid hydrolysis. Examples of suitable biomass sources include but are not limited to wheat straw, barley straw, rice straw, corn stover, sugarcane, bagasse, etc.

According to the invention, the biomass is pretreated, i.e. the biomass is hydrolyzed using dilute acid. Suitable dilute acids that may be used include but are not limited to sulfuric acid, nitric acid, hydrochloric acid, and phosphoric acid. In preferred embodiments, the acid is sulfuric acid.

By "dilute" acid we mean acid present at a concentration in the range of from about 0.05% w/v to about 5% w/v, or from about 0.1% w/v to about 2% w/v, and preferably about 1% w/v.

The procedure for pretreating the biomass is generally carried out by mixing the biomass with acid under conditions that permit the acid to hydrolyze the hemicellulose components of the biomass, and optionally, the cellulose as well, e.g. at a final pH of from about 1.1 to about 1.5; with the amount of acid ranging from about 0.1 to about 2 weight % based on dry biomass; at a temperature of from about 160° C. to about 220° C.; and for periods of time ranging from about seconds to about minutes (Mosier et al., 2005). Descriptions of dilute acid treatment of biomass may also be found, for example, in: McMillan (1992), Saeman (1945), Jacobsen and Wyman (2000), Yat et al. (2008), Chen et al. (1996) and issued U.S. Pat. Nos. 7,993,463 and 5,536,325, the entire contents of which are hereby incorporated by reference.

One advantage of the invention is that with most yeast strains, detoxification of the biomass hydrolysate prior to introduction of the yeast is not necessary. Therefore, in some embodiments of the invention, this step is advantageously eliminated. Hence, in one embodiment, one oleaginous yeast strain is added to the hydrolysate under conditions that allow the yeast to ferment the sugars produced during the pretreatment to form lipids, without detoxification (e.g. overliming). Those of skill in the art will recognize that such processes are generally carried out using fermentation tanks using media such as pretreated lignocellulosic hydrolysate; at pH values in the range of from about 1.1 to about 1.5; at temperatures ranging from about 160° C. to about 220° C.; and for periods of time ranging from about 24 hours to about 14 days, or from about 2-10 days, or even from about 5 to about 8 days, e.g. for about 5, 6, 7, or 8 days or longer.

However, in some embodiments, particularly if the yeast *R. toruloides* is utilized, or if other yeast strains that are determined to be sensitive to the toxic products in the pretreated biomass are utilized, or if otherwise desired (e.g. to affect the type of sugars that remain in the hydrolysate, to facilitate handling or disposal, to prepare for later processing steps, etc.), the pretreated biomass is detoxified. This may be accomplished using lime before introducing yeast into the hydrolysate, or by other methods (e.g. see issued U.S. Pat. No. 7,067,303, the entire contents of which are herein incorporated by reference). Those of skill in the art are readily able to identify yeasts that require detoxification or which are more productive when the hydrolyzed biomass is detoxified, e.g. by measuring the growth rate of the yeast and/or the yield of a desired product with and without detoxification, etc.

If detoxification is carried out, this may be accomplished according to methods that are known in the art, briefly, the original hydrolysate was first heated to 42° C. while stirring using a stir bar. At this time, calcium hydroxide was then added to increase the pH to 10.0 in a process called overliming. The temperature of the hydrolysate increased to 50-52° C. by addition of calcium hydroxide, and thereafter the mixture was maintained at 50° C. and stirred for 30 min using the heater stir plate, followed by filtration using a 0.22 μm membrane (Millipore, Mass.), and the filtrate was allowed to cool to 30° C. The filtrate was then re-acidified to pH 5.5 with sulfuric acid, followed by 0.22 μm filtration to remove any precipitate formed. This detoxified liquid hydrolysate was then ready for use as a fermentation substrate. This process is described e.g. in issued U.S. Pat. No. 7,932,065, the complete contents of which is herein incorporated by reference, and in Martinez et al. (2001).

Once detoxification is complete, one or more (e.g. at least one) suitable yeast strain is added to the detoxified biomass and fermentation is allowed to proceed as described above.

Yeast strains that are employed in the practice of the invention include any of those which are known to produce oils (lipids), i.e. they are oleaginous yeasts. Exemplary oleaginous yeast genera include but are not limited to *Cryptococcus, Rhodotorula, Rhodosporidium, Lipomyces*, and *Yarrowia*. Exemplary oleaginous yeast species include but are not limited to *Cryptococcus curvatus, Rhodotorula glutinis, Rhodosporidium toruloides, Lipomyces starkeyi* and *Yarrowia lipolytica*. In a preferred embodiment, the yeast is a *Cryptococcus* species such as *Cryptococcus curvatus*.

Lipids that can be synthesized and accumulated by oleaginous yeasts using the methods of the invention include but are not limited to: palmitic (C16:0), stearic (C18:0), oleic (C18:1), linoleic (C18:2), linolenic (C18:3), arachidic (C20:0) and others.

The lipids that are generated using the methods of the invention may be used for any suitable purpose. In one embodiment, they are used to produce biofuel. By "biofuel" we mean a fuel made from biologic materials. Exemplary biofuels that may be produced using the lipids generated as described herein include but are not limited to renewable gasoline and diesel, jest fuel and biodiesel. Those of skills in the art are familiar with the production of biofuel from lipids such as microbial generated lipids. Briefly, the process involves dilute acid pretreatment of wheat straw, separation of the liquid hydrolysate and residual solids, detoxification of the hydrolysate by overliming if required, and fermentation of the hydrolysate to form oils as described herein. After extraction, the oils may be used to form biofuel (e.g. methane, biodiesel, bioethanol and other alcohols, etc.) as described, for example, in issued U.S. Pat. Nos. 7,905,930 and 7,977,076 (Oyler), the complete contents of which are hereby incorporated by reference.

Residual solids and non-hydrolyzed cellulose from the dilute acid hydrolysis step may also be separated from the hydrolysate and used for other suitable purposes, e.g. for the production of biofuels and biochemicals, generally after further hydrolysis (usually under harsher conditions) and/or enzymatic breakdown.

The foregoing examples are intended to illustrate various embodiments of the invention but should not be interpreted as limiting in any way.

EXAMPLES

Example 1

Chemical Compositions of NDLH and DLH

The chemical compositions of non-detoxified liquid hydrolysate (NDLH) and detoxified liquid hydrolysate (DLH) are shown in Table 1. The concentrations of monosaccharides in dilute acid pretreated wheat straw hydrolysates varied among results reported, which is attributable to the different origins and sources of wheat straws rather than to pretreatment conditions. Pentoses (arabinose and xylose) and hexoses (galactose and glucose) were the main monosaccharides in the hydrolysates. Besides sugar monomers, acetic acid formed by deacetylation of hemicelluloses was the most abundant with a concentration of 4.03 g/L. Furfural and hydroxymethylfural (HMF), which resulted from the degradations of pentoses and hexoses respectively, were detected in low concentrations. The concentration of the pentoses was about three times as high as that of the hexoses. During the overliming process, to reduce sugar losses, the shift to higher pH must be kept brief to minimize pentose decomposition (Fein et al., 1984). Conflicting literature exists that shown increased loss of all sugars with increasing overliming pHs (Mohagheghi et al., 2006). Thus, the target overliming pH was determined at about 10.0. However, pH values in the range of bout 8-12 may be used, e.g. about 8, 9, 10, 11, 12, etc. Actually the overliming detoxification resulted in the loss of arabinose (21.1%), galactose (35.0%), glucose (14.2%), and xylose (28.6%). And the xylose loss during the overliming was in accordance with those from 7% to 34% reported by Mohagheghi et al. (2006). After the detoxification the acetic acid was still retained in the hydrolysates while both furfural and HMF were almost removed completely.

TABLE 1

Monosaccharide's concentrations in the original hydrolysates

| Monosaccharide | Concentration (g/L) | |
|---|---|---|
| | NDLH | DLH |
| Arabinose | 4.73 | 3.73 |
| Galactose | 1.23 | 0.80 |
| Glucose | 3.67 | 3.15 |
| Xylose | 19.6 | 14.0 |
| Acetic acid | 4.03 | 4.16 |
| Furfural | 0.44 | 0.03 |
| HMF | 0.05 | 0.02 |

Example 2

Effects of Yeast Strains on Biomass and Lipid Production with NDLH and DLH

*Y. lipolytica, C. curvatus, R. glutinis, R. toruloides* and *L. starkeyi* were applied to the fermentation for microbial lipid accumulation due to their physiological oil-producing capacities with pentoses. After 6 days' incubation, there were little monosaccharides detected in the broth. The four yeast strains were able to grow in both DLH and in NDLH except that *R. toruloides* could only survive in the DLH. Additionally there were precipitants generated simultaneously with the yeasts growth, which had not been reported before.

As seen in Table 2, under the existence of both yeast cell mass and precipitants, the highest biomass reached 17.2 g/L in NDLH and 15.6 g/L in DLH by *C. curvatus* with the lipid contents of 33.5% and 27.1%, respectively. The lipid yields (WL) of all the yeast strains except *R. toruloides* were slightly higher in NDLH than DLH. This indicated the non-detoxified hydrolysates had no negative impact on lipid accumulation of the four yeasts. However, Huang et al. (2009) reported that detoxification pretreatment improved the fermentability of the hydrolysate significantly by *T. fermentans*. It demonstrated that different oleaginous yeasts presented different tolerance degrees of inhibitors. That is to say, under the concentrations listed, the *Y. lipolytica, C. curvatus, R. glutinis* and *L. starkeyi* could survive and produce lipids unrestrictedly in the presence of acetic acid, furfural and HMF.

Additionally, there are large differences in lipid yields among the strains. *Y. lipolytica* had the poorest lipid yields, which were 1 g/L in both NDLH and DLH, and the highest lipid yields were 5.77 g/L in NDLH and 4.22 g/L in DLH by *C. curvatus*. As shown in Table 3 and 4, the main acids for all the yeast strains were palmitic (C16:0), stearic (C18:0), oleic (C18:1), and linoleic (C18:2). The fatty acid compositions were different among the yeast strains although little composition changes were observed between the same yeast strain growing in NDLH and DLH. And the degrees of unsaturation (Δ/mole) (Kates and Baxter, 1962), ranging from 0.53 to 0.97, also exhibited differences on fatty acid compositions of each yeast strain.

Furthermore, the total reducing sugar and inhibitors consumption in the NDLH as well as lipid yields of the biomass were determined as shown in the FIG. 1. Acetic acid and furfural were almost completely assimilated within the $1^{st}$ day of the fermentation period, and most of the total reducing sugars were depleted within the first two days. The lipid yields were constant at about 5.2 g/L from the $2^{nd}$ day to the $7^{th}$ day.

TABLE 2

Effect of yeast strains on cell growth and lipid accumulation with NDLH and DLH

| | Biomass* (g/L) | | Lipid content** (%) | | Lipid yield (g/L) | |
|---|---|---|---|---|---|---|
| Strain | NDLH | DLH | NDLH | DLH | NDLH | DLH |
| Y. lipolytica | 7.82 | 7.17 | 4.60 | 4.36 | 0.38 | 0.31 |
| C. curvatus | 17.2 | 15.6 | 33.5 | 27.1 | 5.77 | 4.22 |
| R. glutinis | 13.9 | 11.8 | 25.0 | 20.7 | 3.46 | 2.45 |
| R. toruloides | N/D | 9.87 | N/D | 24.6 | N/A | 2.45 |
| L. starkeyi | 14.7 | 12.7 | 31.2 | 29.1 | 4.57 | 3.71 |

The experiments were conducted at 28° C. and 200 rpm for 6 days.
*, **determined on the mixture of cell mass and precipitants
N/D: not detected
N/A: not available

TABLE 3

Fatty acid composition of lipid accumulated on NDLH

| | Fatty acid compositions (%) | | | | |
|---|---|---|---|---|---|
| Strain | C16:0 | C18:0 | C18:1 | C18:2 | Δ/mole [a] |
| Y. lipolytica | 6.02 | 2.03 | 56.0 | 19.9 | 0.96 |
| C. curvatus | 25.9 | 15.2 | 47.7 | 6.42 | 0.61 |
| R. glutinis | 23.5 | 8.99 | 43.4 | 15.4 | 0.74 |
| R. toruloides | | | N/A | | |
| L. starkeyi | 36.2 | 4.45 | 46.3 | 3.44 | 0.53 |

[a] The number of double bonds per mole

TABLE 4

Fatty acid composition of lipid accumulated on DLH

| | Fatty acid compositions (%) | | | | |
|---|---|---|---|---|---|
| Strain | C16:0 | C18:0 | C18:1 | C18:2 | Δ/mole |
| Y. lipolytica | 5.71 | 0.78 | 55.3 | 20.9 | 0.97 |
| C. curvatus | 27.0 | 15.3 | 45.0 | 7.29 | 0.60 |
| R. glutinis | 22.4 | 9.28 | 42.7 | 17.0 | 0.77 |
| R. toruloides | 19.8 | 5.88 | 53.4 | 13.5 | 0.80 |
| L. starkeyi | 37.1 | 5.50 | 45.1 | 4.85 | 0.55 |

[a] The number of double bonds per mole

REFERENCES

Agbogbo, F. K., Coward-Kelly, G, 2008. Cellulosic ethanol production using the naturally occurring xylose-fermenting yeast, *Pichia stipitis. Biotechnology Letters*, 30, 1515-1524.

Ahring, B. K., Licht, D., Schmidt, A. S., Sommer, P., Thomsen, A. B., 1998. Production of ethanol from wet oxidized wheat straw by *Thermoanaerobacter mathranii*. *Bioresource Technology*, 68, 3-9.

Chen, R., Lee, Y., Torget, R., 1996. Kinetic and modeling investigation on two-stage reverse-flow reactor as applied to dilute-acid pretreatment of agricultural residues. *Applied Biochemistry and Biotechnology*, 57-58, 133-146.

FAO, 2007. Food and Agriculture Organization of the United Nations.

Fein, J. E., Tallim, S. R., Lawford, G. R., 1984. Evaluation of D-xylose fermenting yeasts for utilization of a wood-derived hemicellulose hydrolyzate. *Canadian Journal of Microbiology*, 30, 682-90.

Fu, N., Peiris, P., 2008. Co-fermentation of a mixture of glucose and xylose to ethanol by *Zymomonas mobilis* and *Pachysolen tannophilus*. *World Journal of Microbiology & Biotechnology*, 24, 1091-1097, Huang, C., Zong, M.-h., Wu, H., Liu, Q.-p., 2009. Microbial oil production from rice straw hydrolysate by Trichosporon fermentans. *Bioresource Technology*, 100, 4535-4538.

Jacobsen, S., Wyman, C., 2000. Cellulose and hemicellulose hydrolysis models for application to current and novel pretreatment processes. *Applied Biochemistry and Biotechnology*, 84-86, 81-96.

Kates, M., Baxter, R. M., 1962. Lipid composition of mesophilic and psychrophilic yeasts (Candida species) as influenced by environmental temperature. *Canadian Journal of Biochemistry and Physiology*, 40, 1213-27.

Martinez, A., Rodriguez, M. E., Wells, M. L., York, S. W., Preston, J. F., Ingram, L. O., 2001. Detoxification of Dilute Acid Hydrolysates of Lignocellulose with Lime. *Biotechnology Progress*, 17, 287-293.

McMillan, J. D., 1992. Process for Pretreating Lignocellulosic Biomass: A Review National Renewable Energy Laboratory (NREL). *NREL/TP*-421-4978.

Mohagheghi, A., Ruth, M., Schell, D. J., 2006. Conditioning hemicellulose hydrolysates for fermentation: Effects of overliming pH on sugar and ethanol yields. *Process Biochemistry* (Amsterdam, Netherlands), 41, 1806-1811.

Montane, D., Farriol, X., Salvado, J., Jollez, P., Chornet, E., 1998. Application of steam explosion to the fractionation and rapid vapor-phase alkaline pulping of wheat straw. *Biomass and Bioenergy*, 14, 261-276.

Mosier, N., Wyman, C., Dale, B., Elander, R., Lee, Y. Y., Holtzapple, M., Ladisch, M., 2005. Features of promising technologies for pretreatment of lignocellulosic biomass. *Bioresource Technology*, 96, 673-686.

Olsson, L., Hahn-Haegerdal, B., 1996. Fermentation of lignocellulosic hydrolyzates for ethanol production. *Enzyme and Microbial Technology*, 18, 312-31.

Saeman, J. F., 1945. Kinetics of Wood Saccharification—Hydrolysis of Cellulose and Decomposition of Sugars in Dilute Acid at High Temperature. *Industrial & Engineering Chemistry*, 37, 43-52.

Saha, B. C., Iien, L. B., Cotta, M. A., Wu, Y. V., 2005. Dilute acid pretreatment, enzymatic saccharification and fermentation of wheat straw to ethanol. *Process Biochemistry* (Oxford, United Kingdom), 40, 3693-3700.

Yat, S. C., Berger, A., Shonnard, D. R., 2008. Kinetic characterization for dilute sulfuric acid hydrolysis of timber varieties and switchgrass. *Bioresource Technology*, 99, 3855-3863.

The invention claimed is:

1. A method of producing lipids, comprising the steps of
    hydrolyzing biomass with dilute acid to faun a hydrolysate containing sugars;
    culturing at least one species of oleaginous yeast in the hydrolysate under conditions that allow said oleaginous yeast to produce and accumulate lipids; and
    extracting said lipids from said oleaginous yeast,
    wherein said dilute acid is present at a concentration of 0.05% w/v to 2% w/v.

2. The method of claim 1, wherein said oleaginous yeast is selected from the group consisting of *Cryptococcus curvatus, Rhodotorula glutinis, Lipomyces starkeyi* and *Yarrowia lipolytica*.

3. The method of claim 1, wherein said method further comprises the step of detoxifying said hydrolysate prior to said step of culturing.

4. The method of claim 3, wherein said oleaginous yeast is *Rhodosporidium toruloides*.

5. The method of claim 1, wherein said biomass is lignocellulosic biomass selected from the group consisting of wheat straw, grass straw, barley straw, corn stover and sugarcane bagasse.

6. The method of claim 1, wherein said dilute acid is dilute sulfuric acid.

7. The method of claim 1, further comprising the step of harvesting said oleaginous yeast prior to said step of extracting.

8. The method of claim 1, wherein said oleaginous yeast is *Cryptococcus curvatus*.

9. A method of producing biofuel, comprising the steps of
    hydrolyzing biomass with dilute acid to form a hydrolysate containing sugars;
    culturing at least one species of oleaginous yeast in said hydrolysate under conditions that allow said oleaginous yeast to produce and accumulate lipids;
    extracting said lipids from said oleaginous yeast; and
    producing biofuel from said lipids extracted in said extracting step,
    wherein said dilute acid is present at a concentration of 0.05% w/v to 2% w/v.

10. The method of claim 9, wherein said oleaginous yeast is selected from the group consisting of *Cryptococcus curvatus, Rhodotorula glutinis, Lipomyces starkeyi* and *Yarrowia lipolytica*.

11. The method of claim 9, wherein said method further comprises the step of detoxifying said hydrolysate prior to said step of culturing.

12. The method of claim 9, wherein said biofuel is renewable gasoline, diesel, jet fuel, and biodiesel.

13. The method of claim 9, further comprising the step of harvesting said oleaginous yeast prior to said step of extracting.

14. The method of claim 9, wherein said oleaginous yeast is *Cryptococcus curvatus*.

15. The method of claim 1, wherein said step of hydrolyzing is carried out for a period of time ranging from seconds to minutes.

16. A method of producing lipids, comprising the steps of
    hydrolyzing biomass with dilute acid to form a hydrolysate, wherein the step of hydrolyzing produces at least 4 g/l of acetic acid in the hydrolysate;

culturing at least one species of oleaginous yeast in the hydrolysate under conditions that allow said oleaginous yeast to produce and accumulate lipids; and extracting said lipids from said oleaginous yeast, wherein said dilute acid is present at a concentration of 0.05% w/v to 2% w/v.

* * * * *